(12) United States Patent
Bayon et al.

(10) Patent No.: US 6,706,684 B1
(45) Date of Patent: Mar. 16, 2004

(54) METHOD FOR PREPARING A COLLAGEN MATERIAL WITH CONTROLLED IN VIVO DEGRADATION

(75) Inventors: Yves Bayon, Villeurbanne (FR); Philippe Gravagna, Irigny (FR); Jean-Louis Tayot, La Tour de Salvagny (FR)

(73) Assignee: Imedex Biomateriaux, Trevoux (FR)

( * ) Notice: Subject to any disclaimer, the term of this patent is extended or adjusted under 35 U.S.C. 154(b) by 0 days.

(21) Appl. No.: 09/856,858

(22) PCT Filed: Nov. 9, 1999

(86) PCT No.: PCT/FR99/02746

§ 371 (c)(1),
(2), (4) Date: May 29, 2001

(87) PCT Pub. No.: WO00/32246

PCT Pub. Date: Jun. 8, 2000

(30) Foreign Application Priority Data

Nov. 30, 1998 (FR) .............................................. 98 15072

(51) Int. Cl.[7] ............................................. A61K 38/00
(52) U.S. Cl. ........................................................ 514/2
(58) Field of Search ...................... 623/11–16; 204/159; 523/105–6, 111; 524/17–18; 514/2

(56) References Cited

U.S. PATENT DOCUMENTS

| | | | | |
|---|---|---|---|---|
| 3,808,113 A | * | 4/1974 | Okamura et al. ............ 427/493 |
| 5,035,715 A | * | 7/1991 | Smestad et al. ............. 424/423 |
| 5,733,337 A | * | 3/1998 | Carr et al. .................. 435/325 |
| 6,391,939 B2 | * | 5/2002 | Tayot et al. ................. 523/105 |

* cited by examiner

*Primary Examiner*—Karen Cochrane Carlson
*Assistant Examiner*—Sheridan K Snedden
(74) *Attorney, Agent, or Firm*—Larson & Taylor PLC

(57) ABSTRACT

The invention concerns a method for preparing a non-toxic, sterile, biocompatible, crosslinked collagen material with controlled in vivo biodegradation speed. It consists in subjecting a collagen constituent, either to beta radiation, or to gamma radiation. The collagen material obtained is biodegradable in a few days depending on the type of irradiation used.

33 Claims, No Drawings

METHOD FOR PREPARING A COLLAGEN MATERIAL WITH CONTROLLED IN VIVO DEGRADATION

The present invention relates to a process for preparing a collagenic material making it possible to control the rate of in vivo biodegredation of this material.

It relates more particularly to a process for treating a collagenic component making it possible to obtain materials whose stability and mechanical properties can be varied depending on the conditions of said treatment, said materials being suitable for diverse biomedical applications of collagen.

Collagen-based biomaterials are currently used in many applications, having the major advantage of being resorbable. However, depending on their applications, it is necessary to control their biological degradation. This is because the mechanical properties of the implanted collagenic material have to deteriorate progressively and said material must finally be entirely digested over a defined period.

Depending on the applications of these collagen-based biomaterials, the degradation of the latter must in general take place over a time ranging from a few days to a few weeks.

To achieve these objectives, the collagen properties may be modified in several possible ways. Thus, it is known in the art to carry out treatments resulting in the formation of ionic bonds, hydrogen bonds or covalent bonds (Chvapil et al., in *International Review of Connective Tissue Research*, Vol. 6, ed. D. A. Hall and D. S. Jackson, Academic Press, UK, 1973, 1–61).

The creation of intermolecular links increases the biodegradation time of the collagenic material and the mechanical strength of the collagen fibers, while reducing the water absorptivity, the solubility and the rate of enzymatic degradation of these fibers (Pachence et al., *Medical Device & Diagnostic Industry*, 1987, 9, 46–55).

Thus, processes have been proposed in the art which allow the collagen to be crosslinked either by physical methods or by chemical methods.

The chemical methods use crosslinking agents such as aldehyde compounds, among which may be mentioned, in particular, formaldehyde, glutaraldehyde, succinaldehyde, glyoxal and acrolein, or else carbodiimides, diisocyanates and azide derivatives (Pachence et al., *Medical Device & Diagnostic Industry*, 1987, 9, 46–55; Weadock et al., *Biomat. Med. Dev. Art. Org.*, 1983–84, 11, 293–318; BIO-ETICA and INSERM, FR 2 617 855).

Aldehyde compounds are, to be sure, the most widely used crosslinking agents but they generate potentially cytotoxic biomaterials.

It is desirable to introduce as few chemicals as possible into an implantable biomaterial, since these additives cause complications and regulatory constraints of increasing severity in order to demonstrate the lack of toxicity of such chemicals.

Moreover, a process is known in the prior art for modifying the collagen by forming aldehyde functions within the collagen itself, by oxidative scission using periodic acid or one of its salts, this treatment crosslinking the collagen at neutral or basic pH (M. Tardy and J. L. Tayot, U.S. Pat. No. 4,931,546).

Finally, it has also been proposed in the prior art to modify the properties of the collagen by functionalizing the amino and carboxyl groups of the amino acids that it contains. According to this approach, charge and polarity modifications may thus slow down or accelerate the degradation of collagen (Green et al., *Biochem. J.*, 1953, 154, 181–7; Gustavson, *Ark. Kemi.*, 1961, 55, 541–6).

As regards the physical methods, these include dehydration, aging, heating in the absence of moisture, and irradiation by ultraviolet rays or by beta or gamma rays.

Of these, irradiation treatment with beta or gamma rays is used to sterilize dehydrated collagenic materials, but, in the light of the existing literature, results in materials whose strength cannot easily be predicted.

The various parameters that can influence this type of treatment are not sufficiently well known to allow the quality of the resulting collagenic biomaterials to be controlled, particularly from the point of view of their mechanical strength and their rate of biodegradation (Sintzel et al., *Drug Dev. Ind. Pharm.*, 1997, 23, 857–878).

U.S. Pat. No. 5,035,715 describes irradiation by gamma rays of a substantially moisture-free mixture of collagen and a mineral material, thereby obtaining a certain amount of crosslinking.

Patent EP 0 351 296 describes gamma irradiation of collagen beads, making it possible to increase their density.

Application WO 95/34332 describes the sterilization of a valvular prosthesis made from porcine tissue, and therefore containing collagen, by an electron beam or by X-ray or gamma irradiation. Beta-type electron irradiation of the prosthesis, slightly crosslinked beforehand by a chemical agent, results in less degradation than gamma irradiation. This document does not teach that it is possible to increase the crosslinking and the degradation resistance of such a valve by beta radiation. On the contrary, it teaches that beta radiation has hardly any influence on the crosslinking.

U.S. Pat. No. 5,674,290 describes the sterilization by gamma irradiation of collagenic implants having a high water content, in a sealed envelope transparent to gamma radiation. When this teaching is applied to collagen, the collagen is precrosslinked by a chemical agent. This documents states that, unlike sterilization of a dry collagenic material by gamma irradiation, sterilization of wet collagenic material by gamma radiation only modifies the enzymatic degradability of the material very slightly. The document suggests, erroneously, that sterilization of such a material by an electron beam would be equivalent to sterilization by irradiation by gamma sterilization.

It may therefore be stated that the various known treatments in the prior art allowing certain properties of collagenic materials to be varied either generate undesirable or potential toxicities in the envisioned applications, or are difficult or expensive to implement, or do not allow effective control of the properties of the final material obtained.

It is an objective of the present invention to provide a treatment making it possible to obtain collagenic materials whose rate of degradation in vivo and whose mechanical properties can be varied according to the potential applications of said materials.

It is another objective of the invention to provide a treatment process resulting in a ready-to-use biomaterial by simultaneously carrying out crosslinking and sterilization of the collagenic material.

For this purpose, the subject of the present invention is a process for preparing a crosslinked collagenic material which is biocompatible and nontoxic and has a controlled in vivo rate of biodegradation, characterized in that it comprises subjecting a collagenic component in the wet state to irradiation by beta rays, the collagenic material obtained being sterile and biodegradable over a few days to several weeks.

The subject of the invention is also the aforementioned process characterized in that the collagenic component in the wet state is combined, prior to its irradiation, with a network of collagen fibers, preferably of helical structure.

The invention also relates to materials obtained by the above process.

The invention also relates to a bicomposite which is biocompatible, nontoxic and sterile, has a controlled in vivo rate of biodegradation and is able to be applied by sutures or staples, characterized in that it comprises only, or mainly, two layers intimately associated and crosslinked with interpenetration of the crosslinked networks, one of said layers being formed from a film based on a crosslinked collagenic component and the other from a compacted compress formed from crosslinked collagen fibers rendered insoluble, especially collagen fibers having a helical structure, prepared from collagen dissolved or dispersed in an aqueous solution.

The inventors have discovered, most surprisingly and unpredictably, that the properties of collagenic materials depend on the mode of irradiation—beta or gamma radiation.

In particular, they have discovered that the degree of hydration of the irradiated material itself plays a decisive role in the final properties of the resulting collagenic material.

Specifically, they have found that the results obtained are markedly different according to the nature of the collagenic component treated and according to the irradiation sterilization conditions applied.

Thus, the inventors have presented a treatment allowing both crosslinking and structuring of the collagenic component treated, simultaneously with its sterilization, which, from a wet material substantially free of any complementary crosslinking agent and, preferably, not crosslinked, leads to a ready-to-use material having defined properties, particularly from the standpoint of its mechanical strength and its in vivo degradation time.

According to the invention, the term "structuring", of the collagenic component refers to the balance between the degree of crosslinking and the degree of hydrolysis of said collagenic component, which results in biomaterials of greater or lesser strength.

According to the invention, the nature of the collagenic component refers in particular to its state (moisture content), its pH or its functionalization, as the case may be.

The collagenic component used in the process of the invention is in the wet state. The expression "wet state" is used here to mean a material having a moisture content of greater than 30%, more preferably between 40 and 95%.

By way of comparison, the dry state corresponds to a material whose moisture content is less than 30%, the content preferably being between 5 and 20%.

In this case, the collagen may be present, in the wet state, in the form of a gel or an aqueous solution, or in the partially dehydrated state, in the form of a film, the moisture content being in the latter case close to 30%, unlike the gels and solutions which contain a much larger amount of water.

Whatever its form, the concentration of the collagenic component (solids content) is a minimum of 0.5%, the concentration preferably being greater than 2.5%.

The collagenic component used for the purposes of the invention may consist of or comprise collagen which is either of animal or human origin or is obtained by genetic recombination means. It is preferable to use native collagen, dissolved in acid pH, or else collagen as obtained after a pepsin digestion treatment. In particular, it may be type I bovine collagen or type I or type III human collagen, or else mixtures of the latter in any proportion.

The collagenic component may also consist of or comprise collagen modified by oxidative scission, especially using periodic acid or one of its salts using the technique mentioned above.

It will be briefly recalled that this technique consists in subjecting an acid solution of collagen to the action of periodic acid or one of its salts by mixing it with a solution of this acid or salt with a concentration of between 1M and $10^{-5}$M, preferably between $5 \times 10^{-3}$M and $10^{-1}$M at a temperature close to room temperature, for a time ranging from 10 minutes to 72 hours.

According to the invention, an aqueous acid solution of collagen whose concentration is between 5 and 50 g/l is used, the concentration preferably being 30 g/l.

This treatment causes scissions in certain constituents of the collagen, namely hydroxylisine and the sugars—and thus creates reactive sites without causing crosslinking thereof as long as the pH remains acid.

Oxidative scission of the collagen has the function of allowing subsequent moderate crosslinking of the collagenic material but the invention does not exclude the possibility of carrying out this function by other moderate crosslinking means, for example by beta or gamma radiation, or other moderate crosslinking agents, for example chemical agents at sufficiently low and nontoxic doses.

The collagenic component employed according to the invention may also consist of or comprise collagen that has lost, at least partly, its helical structure, especially by heating to a temperature above 37° C., preferably between 40 and 50° C. for less than an hour.

A final preparation may especially be obtained, which may be likened to gelatin, but the molecular weight of the elementary chains of which is greater than or equal to 100 kDa.

Treating the collagen solution by heating to a temperature of above 37° C. results in the gradual loss of the helical structure of collagen, but the invention does not exclude the possibility of carrying out this function by other physical or chemical means, for example by ultrasound or by the addition of chaotropic agents.

The collagenic component may also be formed from or comprise collagen functionalized at the level of the amino and/or carboxyl functional groups of the amino acids, for example by succinylation or methylation, or by the grafting of fatty acids, or any other method known to chemically modify collagen.

The invention also applies to mixtures of the various aforementioned collagenic components in any proportions.

The collagenic component according to the invention may also contain a macromolecular hydrophilic additive.

According to the present invention, the macromolecular hydrophilic additive has a molecular weight advantageously greater than 3 000 daltons.

Examples of this are synthetic hydrophilic polymers advantageously having a molecular weight of between 3 000 and 20 000 daltons. Polyethylene glycol is particularly preferred.

Other examples are polysaccharides, among which may be mentioned starch, dextran and cellulose, which are preferred.

Provision may also be made to use such polysaccharides in the oxidized form by revealing carboxylic functions in these molecules.

Mucopolysaccharides may also be suitable for purposes of the invention, but these are not preferred as their particular animal origin makes them difficult to prepare while meeting the regulatory standards on traceability.

The hydrophilic additive is selected according to various parameters connected especially with its application, such as its price, its harmlessness, its biodegradability and/or its ability to be easily removed, especially via the kidneys, in the case of therapeutic application.

The concentration of the hydrophilic additive is from 2 to 10 times less than that of the collagenic component.

The process for preparing a collagenic material according to the present invention will be described below in more detail.

The process comprises a step in which the collagenic component as defined above is subjected to irradiation by beta rays with variable doses according to the desired mechanical strength of the final biomaterial and to its in vivo rate of biodegradation.

Advantageously, the collagenic component is treated at neutral pH, preferably between 6.5 and 8, for the purpose of favoring the crosslinking reactions and of obtaining a biomaterial which is biocompatible by virtue of the physiological pH.

The collagenic component is crosslinked/structured by irradiation with beta rays At sterilizing doses, advantageously of about 5 to 50 kGrays, preferably between 25 and 35 kGrays.

Under certain conditions, the doses may be reduced, for example down to 5 kGrays, for materials which are already sterile or have a very low degree of contamination, thereby making it possible to lower the degree of crosslinking.

According to the invention, the beta-irradiation treatment applied to a collagenic component in the wet state makes it possible to obtain a material having a high degradation resistance which is thus biodegradable in vivo over several weeks, whereas exposure to gamma radiation results in a biomaterial having a low degradation resistance, which will thus be biodegradable in vivo over a few days.

These results are the opposite of those obtained for a collagenic component in the dry state, for which irradiation by beta rays results in a biomaterial which will degrade over a few days, whereas gamma irradiation results in a biomaterial which will degrade over a few weeks.

According to an alternative way of implementing the invention, the collagenic component intended to be structured by irradiation is combined beforehand with a network of undenatured collagen fibers, which is advantageously in the form of a compacted compress.

This compress may be prepared from native collagen oxidized using periodic acid or one of its salts.

Fibers are formed from the resulting solution and they are then crosslinked by neutralization.

The oxidized collagen fibers, of helical structure, thus crosslinked are freeze-dried and dehydrated, and then compacted to form the compress.

Next, a solution of collagenic component, prepared as indicated above, is deposited on this compacted fibrous collagen compress.

The assembly is advantageously dried and partially rehydrated in order to increase the concentration of the collagenic component.

Next, the irradiation treatment as described above is carried out.

Thus, the aforementioned assembly is structured/crosslinked, resulting in a bicomposite comprising a layer forming a film based on a crosslinked collagenic component combined with a compacted compress of crosslinked collagen fibers with interpenetration of the crosslinked networks.

In general, this process can be applied to woven or nonwoven compresses of collagen fibers advantageously of helical structure.

The collagenic materials obtained by the process of the invention are useful for the prevention of post-operative adhesion and/or the healing of wounds.

Such materials are particularly useful for promoting the healing of skin wounds and surgical wounds. Their biocompatible nature makes them very easily colonizable by the cells of the various types of tissue with which they are brought into contact.

In the case of internal wounds, it has been found that this healing takes place harmoniously without resulting in anarchic fibrous tissue proliferation responsible for post-operative adhesion.

The healing activity of these materials may, of course, be enhanced by the addition of cell differentiation and growth factors.

The materials according to the invention are therefore recommended for rapidly ensuring high-quality healing, as close as possible to the initial anatomy.

The collagenic materials combined with a network of collagen fibers are also useful for wound healing, as indicated above. They have the advantage of being able to be applied by sutures and by staples, given their very high strength resulting from the irradiation with beta rays.

These materials may also be used for tissue or wall replacement (for example for esophageal walls, intestinal walls, etc.) or for filling tissues or walls (in the event of partial ablation of part of a tissue or wall).

EXAMPLES

Example 1

Structuring of a Heated Collagen Gel

An acid solution of type I bovine collagen, having a concentration of 16%, was prepared by dissolving the acid collagen powder in demineralized ultrafiltered water, at a temperature of between 40 and 60° C., for a time of less than 30 minutes. The solution was neutralized to a pH of 7.45 by the addition of normal sodium hydroxide as soon as the collagen solution was sufficiently fluid, i.e. 5 to 10 minutes after putting the collagen into water, in order to prevent hydrolysis of the collagen.

Next, the collagen solution was sterilely filtered over a membrane of 0.22 μm porosity and kept at a temperature between 0 and 10° C. before use.

A final preparation was obtained which may be likened to gelatin, but the molecular weight of the elementary chains of which was greater than or equal to about 100 kDa.

Other sources of collagen known to those skilled in the art may be used to obtain heated collagen as described above in this example.

In the case of type I bovine collagen, it may be acid-soluble (extracted from skins or tendons at acid pH) or dissolved by digestion with pepsin, which facilitates the subsequent sterilizing filtrations of the heated collagen.

The heated collagen solution obtained is then formed by molding, "prilling" (the formation of beads by passing through capillaries and collecting the drops), partial drying (which makes it possible to increase the concentration of the collagenic component) or any other process at a temperature between 40 and 70° C., and is then cooled to a temperature between 0 and 25° C.

The purpose of these treatments is to obtain biomaterials of any form, suitable for the desired applications, such as, for example, capillary tubes, beads, microbeads, capsules and films, possibly containing molecules of therapeutic benefit.

The biomaterial prepared is crosslinked and sterilized either by gamma irradiation or by beta irradiation with a dose of 25 to 35 kGy.

The biomaterial irradiated by gamma rays dissolves in demineralized water, at 37° C., in less than 24 hours.

On the other hand, the treatment by beta irradiation highly crosslinks the biomaterial. The latter does not degrade in demineralized water at 60° C., even after one day. Its water absorptivity is low, even zero. It is less than 10% of the weight of the biomaterial. Its biodegradation in vivo is slow and requires several weeks when the site of implantation of the biomaterial, in an animal, is subcutaneous or in contact with viscera.

According to a variant, this material may be prepared from a solution of native collagen having a concentration of between 0.5 and 3%, containing 5 g/l of NaCl, and not subjected to the heating step so as to maintain the helical structure of the collagen.

Example 2
Structuring of a Partially Rehydrated Collagen Film

The material of Example 1 was prepared in the form of a film 2 mm in thickness, without any chemical additive.

Before the final treatment step by irradiation, the film obtained was dehydrated in a stream of dry air and filtered for 24 hours.

The dry film obtained was then rehydrated for 5 to 10 minutes in distilled water.

The partially rehydrated film was packaged in a package impermeable to water vapor, and then subjected to the beta or gamma irradiation treatment at a dose of 25 to 35 kilograys.

The film finally obtained measured between 0.5 and 1 mm in thickness, depending on the rehydration time applied previously. Its collagen content was between 30 and 60%.

The material sterilized by beta irradiation was highly resistant to stretching forces and degraded in vivo, subcutaneously, over more than 3 weeks.

The material sterilized by gamma irradiation had little resistance to stretching forces, spontaneously swelled in contact with water at 37° C. and degraded in vivo after implantation in less than one week.

As a variant, this material may be prepared from a solution of native collagen having a concentration of between 0.5 and 3%, containing 5 g/l of NaCl, and not subjected to the heating step so as to maintain the helical structure of the collagen.

Example 3
Production of a Suturable Material by Combination of the Collagenic Material of Example 2 with a Network of Collagen Fibers of Helical Structure
a) Preparation of the Network of Collagen Fibers An acid solution of type I bovine collagen having a concentration of 1% was prepared by dissolving the acid powder in ultrafiltered demineralized water at 20° C.

Orthoperiodic acid was added to this solution, in the dark, so as to obtain a final concentration of $5 \times 10^{31}$ $^3$M for the purpose of preparing oxidized collagen fibers according to Patent FR 2 601 371.

After 2 hours' treatment, this solution was injected into a series of parallel capillaries about 300 microns in internal diameter, which thus produced fine collagen tubes which were cut into units of 4 cm in length by an automatic cutting device. These fine collagen capillaries were collected, loose, in an alkaline buffer solution of 0.05M sodium hydroxide at 9.3 pH, to which 30% ethanol was added.

Under these conditions, the oxidized collagen crosslinked immediately and the collagen tubes became insoluble. The tubes thus crosslinked were washed in successive baths of ultrafiltered water. Next, a suspension of these fibers was made, containing 2% of collagenic solids, to which 1% glycerol was added, and spread out into plaques 5 mm in thickness.

The plaques were then freeze-dried and the dehydrated compresses were compacted by applying pressure, in order to obtain a thickness from 1 to 2 mm.
b) Preparation of the Heated Collagen Solution A heated 5% collagen solution was produced as described in Example 1 or 2.
c) Combining of the Above Two Materials The solution prepared in "b)" was poured onto the compacted compress described in section "a)" in an amount of approximately 0.2 ml/cm².

Next, the assembly was dried in a sterile laminar flow for 24 hours.

Next, the composite was partially rehydrated by immersion in water for 10 minutes.

The material was packaged in a package impermeable to water vapor and sterilized by beta irradiation (beam of accelerated electrons).

An extremely stretch-resistant material was obtained, the mechanical properties of which made it able to be used with the surgical techniques of suturing and stapling.

This material consists only of collagen, without any chemical additive. It is nontoxic, fully tolerated by the body and can be used as a substitute for the animal tissues currently used by surgeons (fascia lata, dura mata, etc.) in tissue and wall replacement or filling applications, or for healing applications.

Example 4
Structuring of Collagenic Hydrocolloids Consisting of Oxidized Native Collagen Fibers The collagenic hydrocolloids were produced from native bovine collagen, not digested by pepsin, and oxidized by periodic acid according to the process described in U.S. Pat. No. 4,931,546.

Fibers of type I native collagen extracted from the skins of young calves were employed. Other collagen sources known to those skilled in the art could have been used.

A 30 g/l collagen solution was prepared by suspension in 0.01N HCl, in a volume of 720 ml. Periodic acid at the final concentration of 8 mM, that is to say 1.83 g/l, was added.

The oxidation was carried out in the dark at a temperature of 22±3° C. for 3 h±30 minutes, with stirring.

Next, the oxidized collagen was precipitated by adding 240 g/l NaCl until a final NaCl concentration of 41 g/l was obtained.

After waiting for 30 minutes, the precipitate was collected by decanting through a cloth screen, of porosity between 20 and 100 μm, and then washed 4 times with a 41 g/l NaCl solution in 0.01N HCl in order to remove any traces of periodic acid or of its derivatives formed during oxidation of the collagen. A 110 g precipitate was obtained.

Next, the sodium chloride was removed by three successive washings of the saline collagen precipitate, using an acetone/water mixture (80/20, m/m).

A final washing with 100% acetone made it possible to obtain 51.5 g of a concentrated acetone precipitate of uncrosslinked, acid oxidized collagen containing no toxic substances due to the use of periodic acid.

The acetone precipitate was taken up in 390 ml of ultrafiltered demineralized (apyrogenic) water at 40° C. for 5 to 10 minutes, in order to obtain a collagen concentration of 4.1%. The mixture was then heated for 30 minutes at 50±5° C.

After use, the oxidized heated collagen solution may be stored at −20° C.

In order to produce the hydrocolloid, a sterile solution of PEG 4000 (polyethylene glycol having a molecular weight of 4 000) was added at 38° C. to the heated oxidized collagen with a final concentration of 4.1%, as prepared above, in order to achieve a final PEG concentration of 1.3% and a final total collagen content of 3.9%. The pH of this solution was then neutralized to 7.3.

The collagen mixture was poured into hydrophobic supports made of polystyrene or PVC, in an amount of 0.2 g/cm$^2$. It was evaporated, in a stream of sterile air, for 18 to 24 hours, at a temperature close to 22° C. The resulting film was rehydrated for 15 to 20 minutes in apyrogenic demineralized water in order to obtain a hydrocolloid. This biomaterial was structured and sterilized by irradiation with beta or gamma rays, at a dose of between 25 and 35 kGy. Its moisture content before sterilization is preferably between 75 and 95%.

The hydrocolloids structured by irradiation using gamma rays disintegrated in less than 24 hours, at 37° C., when they were immersed in apyrogenic demineralized water.

In contrast, beta irradiation, with the abovementioned doses, made it possible to obtain a stronger hydrocolloid which retained its integrity, even after having been immersed in apyrogenic demineralized water at 37° C. for 24 hours.

Example 5
Structuring of Collagenic Hydrocolloids Consisting of Unoxidized Native Collagen Fibers The hydrocolloids described in this example represent a variant of Example 4.

They were prepared from unoxidized heated collagen and PEG 4000 as macromolecular hydrophilic additive.

Acid native bovine collagen I was taken up in ultrafiltered demineralized water to a final concentration of 3%, the water containing 1% PEG 4000. The mixture was kept at 42° C., with stirring, until a homogeneous solution was obtained, that is to say in less than 30 minutes. The mixture was then vacuum-degassed.

Next, this mixture was poured into hydrophobic supports made of polystyrene or PVC, in an amount of 0.27 g/cm$^2$.

It was dried in a stream of sterile air for 18 to 24 hours.

The resulting film was rehydrated for 15 to 20 minutes in a physiological buffer so as to obtain a film of neutral pH, between 7 and 8. For this purpose, a 150 mM phosphate buffer, of 8.2 pH, may be used.

This biomaterial was structured and sterilized by irradiation with beta or gamma rays with a dose of between 25 and 35 kGy. Its moisture content before sterilization is preferably between 75 and 95%.

The properties of the materials obtained were comparable to the materials described in the previous examples. Sterilization by beta irradiation makes the hydrocolloid based on unoxidized native bovine collagen I stronger than sterilization by gamma irradiation.

Example 6
Structuring of Collagenic Hydrocolloids Consisting of Oxidized Pepsinized Bovine Collagen I The hydrocolloids described in this example represent a variant of Examples 4 and 5.

Pepsinized bovine collagen I was used. Type I or III human collagens, or a mixture thereof in any proportions, can be used in the same way.

The collagen was oxidized as described in Example 4 with the following modifications:

The acetone oxidized collagen precipitate was taken up in ultrafiltered demineralized water at 40° C. to a final concentration of 3%. Next, it was heated for 30 minutes at 50° C. The oxidized heated collagen solution was sterilized by filtration over a membrane of 0.45 μm porosity in an oven at 40° C.

PEG 4000 as a 20% aqueous solution was added, at a temperature of 38° C., to the oxidized collagen as prepared above, in order to achieve a final PEG concentration of 1%. The mixture was neutralized to a pH of 7.0 with 0.5N and 0.1N sodium hydroxide. Next, it was spread out in hydrophobic supports made of polystyrene or PVC, in an amount of 0.27 g/cm$^2$.

It was dried in a stream of sterile air for 18 to 24 hours at a temperature close to 22° C. It was then rehydrated in ultrafiltered demineralized water.

This biomaterial was structured and sterilized by irradiation with beta or gamma rays at a dose of between 25 and 35 kGy.

Its moisture content before sterilization is preferably between 75 and 95%.

As for the previous examples carried out on wet biomaterials, beta irradiation resulted in stronger materials than gamma irradiation.

Example 7
Structuring of Collagenic Hydrocolloids Consisting of Unoxidized Heated Pepsinized Type I Collagen The hydrocolloids described in this example represent a variant of Examples 4, 5 and 6.

The collagenic hydrocolloids were produced from type I native bovine collagen digested by pepsin and heated.

Heated type I or III human collagens, or a mixture thereof in any proportions, can be used in the same way.

A 3% solution of collagen, heated and neutralized, to 7.45 pH, prepared according to example 1, was employed.

A concentrated sterile PEG 4000 solution was added, at 42° C., to the heated 3% collagen in order to obtain a final PEG concentration of 0.9% and a final collagen concentration of 2.7%. The pH of the solution was adjusted to 7.0 by addition of concentrated sodium hydroxide solution.

Next, this mixture was poured into hydrophobic supports made of polystyrene or PVC, in an amount of 0.27 g/cm$^2$.

The mixture was dried in a stream of sterile air for 18 to 24 hours at a temperature close to 22° C.

The resulting film was rehydrated for 15 to 20 minutes in ultrafiltered demineralized water.

This biomaterial was structured and sterilized by beta or gamma irradiation with a dose of between 25 and 35 kGy.

Before sterilization, its moisture content was preferably between 75 and 95%.

As for the previous examples, produced from wet biomaterials, gamma irradiation resulted in weaker materials than beta irradiation.

Comparative Example
Structuring of a Dry Collagen Film

A collagen film was produced as described in Patent Application FR 97/11589.

Heated oxidized collagen, prepared according to example 6, was employed.

The collagen used as raw material for the preparation of the heated oxidized collagen was type I bovine collagen, optionally dissolved by digestion in pepsin, and purified by saline precipitations, using the techniques already described. Type I or III human collagens, or a mixture thereof in any proportions, could be used in the same way.

A concentrated sterile solution of PEG 4000 and glycerol was added to a 3% solution of oxidized heated collagen in order to obtain a final PEG concentration of 0.9%, a final glycerol concentration of 0.54% and a final total collagen concentration of 2.7%. The pH of the solution was adjusted to 7.0 by addition of a concentrated sodium hydroxide solution.

This solution was poured as a thin layer, with a density of 0.133 g/cm$^2$, onto a flat hydrophobic support of the PVC or polystyrene type. The film was dried in a stream of sterile air at a temperature close to 22° C.

The average thickness of the film obtained was 40 to 50 μm, with an average moisture content of 10%.

The dry film was irradiated by beta or gamma rays with a dose of between 25 and 35 kGy.

In this case, the dry film irradiated by gamma rays had better mechanical properties than the film irradiated by beta rays, as indicated by the lower degree of swelling of the films treated by gamma rays. Similarly, the in vivo biodegradation of the dry film treated by gamma rays took more than 3 weeks. In contrast, the dry film irradiated by beta rays was "digested" in vivo in less than one week.

| Irradiation mode | Resistance to degradation in acid medium (pH 2) at 37° C. | In vivo biodegradation |
|---|---|---|
| 25–35 kGy beta (beam of accelerated electrons) | | |
| Dry state | low | a few days |
| Wet state | high | several weeks |
| 25–35 kGy gamma (radioactive source) | | |
| Dry state | high | several weeks |
| Wet state | low | a few days |

What is claimed is:

1. A process for preparing a crosslinked collagenic material which is biocompatible and nontoxic and has a controlled in vivo rate of biodegradation, said process comprising the step of:
    subjecting a collagenic component substantially free of any complementary crosslinking agent, in the wet state to irradiation with beta radiation, the collagenic component comprising collagen that has at least partially lost its helical structure by heating above 37° C.,
    the collagenic material obtained being sterile and biodegradable over a few days to several weeks.

2. The process as claimed in claim 1, wherein the collagenic compound has a moisture content of greater than 30%.

3. The process as claimed in claim 1, wherein the collagenic component is in the form of a gel.

4. The process as claimed in claim 1, wherein the collagenic component is in the form of an aqueous solution.

5. The process as claimed in claim 1, wherein the collagenic component has a neutral pH.

6. The process as claimed in claim 1, wherein the concentration of the collagenic component (solids content) is a minimum of 0.5%.

7. The process as claimed in claim 1, wherein the collagen that has at least partially lost its helical structure is formed from unhydrolyzed collagen consisting mostly of α chains.

8. The process as claimed in claim 1, wherein the collagenic component comprises oxidized collagen.

9. The process as claimed in claim 8, wherein the oxidized collagen comprises collagen modified by oxidative scission using periodic acid or one of its salts.

10. The process as claimed in claim 1, wherein the collagenic component comprises collagen functionalized at the level of the amino and/or carboxyl functional groups of the amino acids, said functionalization comprising succinylation, methylation, grafting of fatty acids or any other method to modify collagen.

11. The process as claimed in claim 1, wherein the collagenic component comprises a macromolecular hydrophilic additive.

12. The process as claimed in claim 11, wherein the macromolecular hydrophilic additive has a molecular weight greater than 3,000 daltons.

13. The process as claimed in claim 11, wherein the macromolecular hydrophilic additive is a hydrophilic polymer having a molecular weight of between 3,000 and 20,000 daltons.

14. The process as claimed in claim 11, wherein the macromolecular hydrophilic additive is polyethylene glycol.

15. The process as claimed in claim 11, wherein the macromolecular hydrophilic additive is chosen from polysaccharides comprising starch, dextran and cellulose, and mucopolysaccharides.

16. The process as claimed in claim 15, wherein the macromolecular hydrophilic additive is a polysaccharide in oxidized form.

17. The process as claimed in claim 1, wherein the collagenic component is irradiated with a dose of 5 to 50 kGy.

18. The process as claimed in claim 17, wherein the collagenic component is irradiated with a dose of 20 to 50 kGy.

19. The process as claimed in claim 1, wherein the resulting collagenic material is crosslinked and biodegradable in vivo over several weeks following irradiation of the collagenic component by beta radiation.

20. The process as claimed in claim 1, further comprising the step of combining the collagenic component in the wet state with collagen fibers, prior to its irradiation.

21. The process as claimed in claim 20 wherein the collagen fibers comprise a compress of compacted fibers, obtained from an acid solution of native collagen, said compress of compacted fibers formed by the method comprising the steps of:
    treating native collagen with periodic acid or one of its salts,
    forming collagen fibers from the periodic acid treated collagen,
    crosslinking the collagen fibers by neutralization,
    compressing the resulting crosslinked collagen fibers of helical structure by applying pressure thereby forming a compress,
    depositing a solution of a collagenic component on said compress thereby forming an assembly, and
    irradiating the assembly with beta radiation.

22. A collagenic bicomposite which is biocompatible, nontoxic and sterile, has a controlled in vivo rate of biodegradation and is able to be applied by sutures or staples, said collagenic bicomposite comprising only, or mainly, a first and a second layer intimately associated and crosslinked with interpenetration of the crosslinked networks, the first of said layers being formed from a film based on a crosslinked collagenic component deposited on the second of said layers being formed from a compacted compress formed from crosslinked collagen fibers rendered insoluble.

23. The collagenic bicomposite as claimed in claim 22, wherein the collagenic bicomposite is crosslinked via combining the collagenic component in the wet state with collagen fibers, prior to its irradiation.

24. The collagenic bicomposite as claimed in claim 22, wherein the collagenic component comprises one of (a) collagen that has at least partially lost its helical structure, (b) oxidized collagen, or (c) a macromolecular hydrophilic additive.

25. The process as claimed in claim 1, wherein the collagenic component is not crosslinked.

26. The process as claimed in claim 1, wherein the collagenic compound has a moisture content of greater than 40%.

27. The process as claimed in claim 1, wherein the collagenic compound has a pH comprised between 6.5 and 8, inclusive.

28. The process as claimed in claim 1, wherein the concentration of the collagenic component (solid content) is greater than 2.5%.

29. The process as claimed in claim 1, wherein the collagenic component comprises collagen that has at least partially lost its helical structure by heating between 40 and 50° C.

30. The process as claimed in claim 17, wherein the collagenic component is irradiated with a dose of 25 to 35 kGy.

31. The process as claimed in claim 1, further comprising the step of combining the collagenic component in the wet state with collagen fibers of helical structure prior to its irradiation.

32. The collagenic bicomposite as claimed in claim 23, wherein the collagen fibers have a helical structure.

33. The collagenic bicomposite as claimed in claim 22, wherein said crosslinked collagen fiber having a helical structure formed from collagen dissolved or dispersed in an aqueous solution.

* * * * *